(12) United States Patent
Shelchuk

(10) Patent No.: US 7,223,237 B2
(45) Date of Patent: May 29, 2007

(54) IMPLANTABLE BIOSENSOR AND METHODS FOR MONITORING CARDIAC HEALTH

(75) Inventor: Anne M. Shelchuk, Cupertino, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 406 days.

(21) Appl. No.: 10/830,850

(22) Filed: Apr. 22, 2004

(65) Prior Publication Data

US 2005/0240088 A1   Oct. 27, 2005

(51) Int. Cl.
*A61B 5/00* (2006.01)
(52) U.S. Cl. .................................... 600/309
(58) Field of Classification Search ............... 600/309, 600/325, 333; 607/22
See application file for complete search history.

(56) References Cited

U.S. PATENT DOCUMENTS

| | | | | |
|---|---|---|---|---|
| 4,202,339 | A | 5/1980 | Wirtzfeld et al. | 128/419 |
| 4,940,052 | A * | 7/1990 | Mann et al. | 607/17 |
| 6,049,727 | A * | 4/2000 | Crothall | 600/310 |
| 6,049,728 | A * | 4/2000 | Chou | 600/316 |
| 6,109,098 | A | 8/2000 | Dukhin et al. | 73/64.42 |
| 6,122,536 | A * | 9/2000 | Sun et al. | 600/341 |
| 6,645,144 | B1 | 11/2003 | Wen et al. | 600/437 |
| 7,074,194 | B2 * | 7/2006 | Crosby et al. | 600/508 |
| 2003/0022235 | A1 * | 1/2003 | Dahlen et al. | 435/7.1 |
| 2003/0130570 | A1 | 7/2003 | Krivitski | 600/322 |

OTHER PUBLICATIONS

Dukhin, et al., "Acoustic and Electroacoustic Spectroscopy for Characterizing Concentrated Dispersions and Emulsions", Advances in Colloid and Interface Science 92 (2001) 73-132.

Dunkhin, et al., "Ultrasound for Characterizing Colloids, Particle Sizing, Zeta Potential, Rheology", Dispersion Tehcnology, Inc., NY, USA, First Edition, 2002, 18 pages.

Schneditz, et al., "A Sound-Speed Sensor for the Measurement of Total Protein Concentration in Disposable, Blood-Perfused Tubes", Journal of the Acoustical Society of America, American Institute of Physics, New York, US vol. 86, No. 6, Dec. 1989, pp. 2073-2080.

Wen, et al., "Ultrasonic Imaging of the Electroacoustic Effect in Macromolecular Gels", Ultrasonic Imaging, Dynamedia, Inc., vol. 20, No. 4, Oct. 1998, pp. 288-297.

Savateeva et al., "Optical properties of blood at various levels of oxygenation studied by time resolved detection of laser-induced pressure profiles", Proceedings of SPIE, Biomedical Optoacoustics III, vol. 4618, 2002, pp. 63-75.

* cited by examiner

*Primary Examiner*—Eric Winakur
*Assistant Examiner*—Etsub Berhanu
(74) *Attorney, Agent, or Firm*—Steven M. Mitchell

(57) ABSTRACT

The ability to continuously monitor concentrations of any of a plurality of blood-borne substances, such as proteins, improves patient monitoring and overall care through early detection of cardiac threats. Ultrasound-based technology used in analytical chemistry to determine amounts of particles suspended in a colloidal composition can be employed in an implantable sensor to monitor levels of many different substances in the blood. A sensor system is implanted in or near a blood vessel in the body and generates an electric or acoustic field directed at that blood vessel. A receiver near the generator detects energy emitted once the assaulting field is turned off. Changes in the relative amounts of the substance(s) being monitored appear as changes in the amount of energy emitted once the assaulting field is removed. The sensor may be implemented in an implantable cardiac therapy device. A non-implantable or transcutaneous sensor may also be used to monitor cardiac health.

34 Claims, 13 Drawing Sheets

IMPLANTABLE BIOSENSOR AND METHODS FOR MONITORING CARDIAC HEALTH

BACKGROUND OF THE INVENTION

1. Field of the Invention

This invention relates to electroacoustic technology used in implantable devices.

2. Related Art

When an acoustic field is applied to a colloid containing particles with a charge, the arrangement of solvent molecules surrounding the solute particles (the double-layer) is disrupted. When the acoustic field is removed, the solvent molecules reassemble themselves and give off an electric field proportional to the energy required for the initial disruption of solvent molecules. Alternatively, when a colloid is transiently exposed to a changing electric field, the same disruption of solvent molecules takes place and the reassembly of the double-layer emits an acoustic field. These principles are employed in analytical chemistry to characterize the composition and stability of colloids.

Colloidal chemistry has historically been used for inorganic compounds such as paint, lotions, and other slurries. Organic compounds, however, have not been investigated using these techniques because they were considered too small for colloidal chemistry to be effective.

SUMMARY OF THE INVENTION

Proteins are relatively large particles that have a surface charge distribution. Hence, the analytical chemistry technique can be employed to monitor levels of suspended substances, including proteins, in a biomedical colloid such as blood. Although the description herein will typically refer to detecting levels of proteins in blood, one skilled in the art will recognize that the present invention may also be used to detect other substances in organic fluids.

The present invention provides a biosensor for detecting proteins in blood. The biosensor adapts the techniques from traditional inorganic colloidal chemistry for use in an organic setting. In an embodiment, the biosensor is used in conjunction with an implantable device, such as a pacemaker or implantable cardioverter defibrillator. The biosensor may be physically connected to the implantable device, or it may be separated by a set of transmission lines or by wireless transmission capabilities. In the implantable embodiment, the biosensor is placed near a blood vessel or interstitial fluid, and directs an assaulting field toward the vessel or fluid. The frequency of the assaulting field is chosen based on the protein of interest. The assaulting field may be an acoustic field or an electric field. When the assaulting field is turned off, the fluid surrounding the proteins move to reassemble the double layer. This movement emits a resultant field. If the assaulting field is an acoustic field, the resultant field is an electric field. Conversely, if the assaulting field is an electric field, the resultant field is an acoustic field.

The relative concentration of the protein of interest can be determined from the magnitude of the resultant field. Over time, the relative concentration can be monitored by the implanted device or by a clinician. Depending on the proteins monitored, changes in protein concentration can be indicative of overall cardiac health, including any impending threats to cardiac health. For example, changes in the levels of peptides, such as brain natriuretic peptide ("BNP") and/or atrial natriuretic peptide ("ANP"), may be indicative of impending heart failure exacerbation. In another example, changes in the levels of C-reactive protein, CK-MB, ischemia-modified albumin, Troponin I, Troponin T, Troponin C, and/or myoglobin may be indicative of myocardial ischemia and impending arrhythmia. Cardiac therapy may be administered in response to such changes in protein concentration.

In another embodiment, the biosensor is a transcutaneous biosensor, meaning that it measures the concentration of the substance of interest in vivo by transmitting an assaulting field through the skin.

In another embodiment, the biosensor is a standalone sensor. In this embodiment, the biosensor measures protein concentrations in external samples, such as a blood sample.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

The present invention will be described with reference to the accompanying drawings. The drawing in which an element first appears is typically indicated by the leftmost digit(s) in the corresponding reference number.

DETAILED DESCRIPTION OF THE INVENTION

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein. Before describing the invention in detail, it is helpful to describe an example environment in which the invention may be implemented.

A. Implantable Cardiac Therapy Devices

Figure 1A:
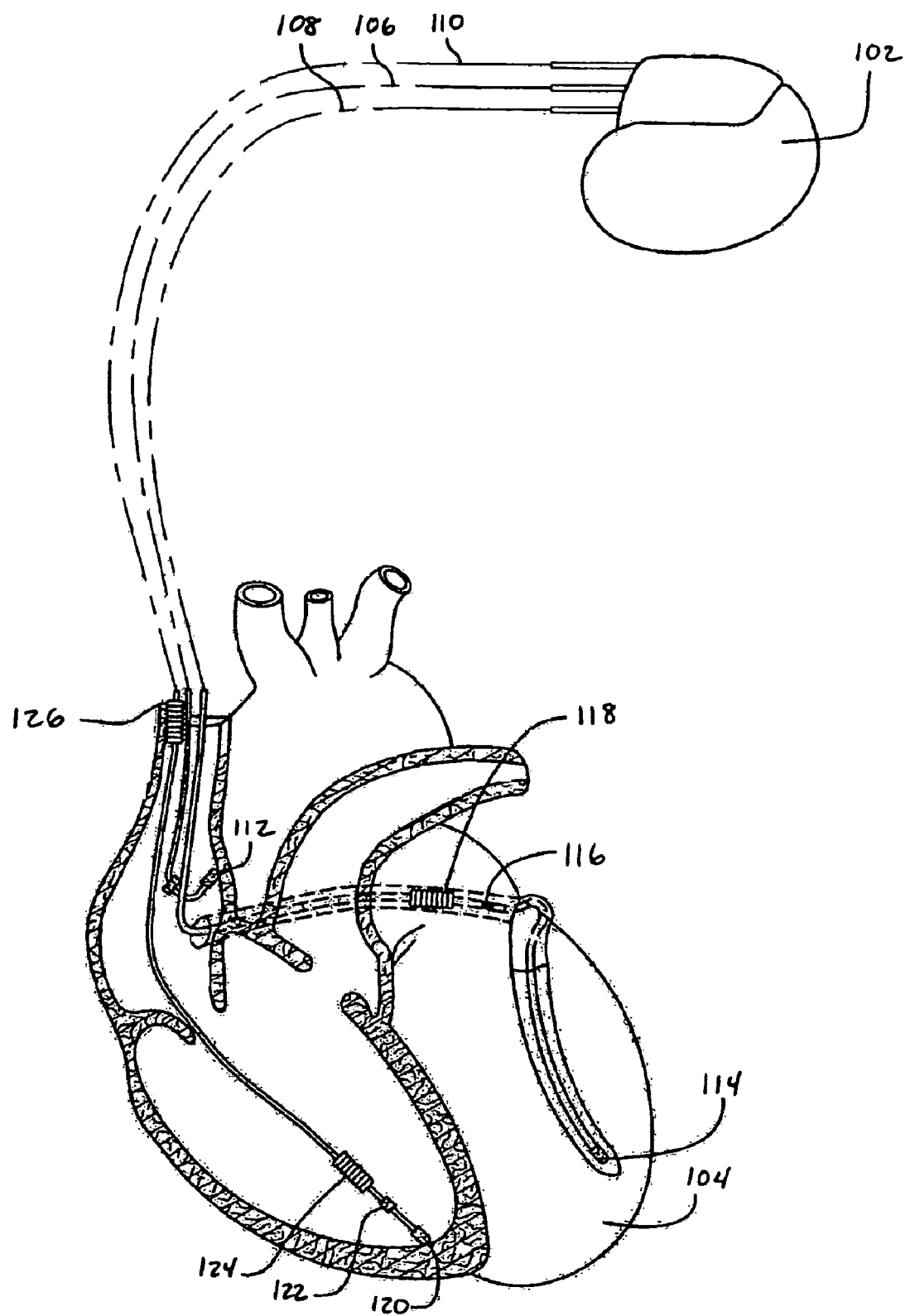
FIG. 1A is a diagram of an example implantable cardiac therapy device ("ICTD") used in the present invention.
Figure 1B:
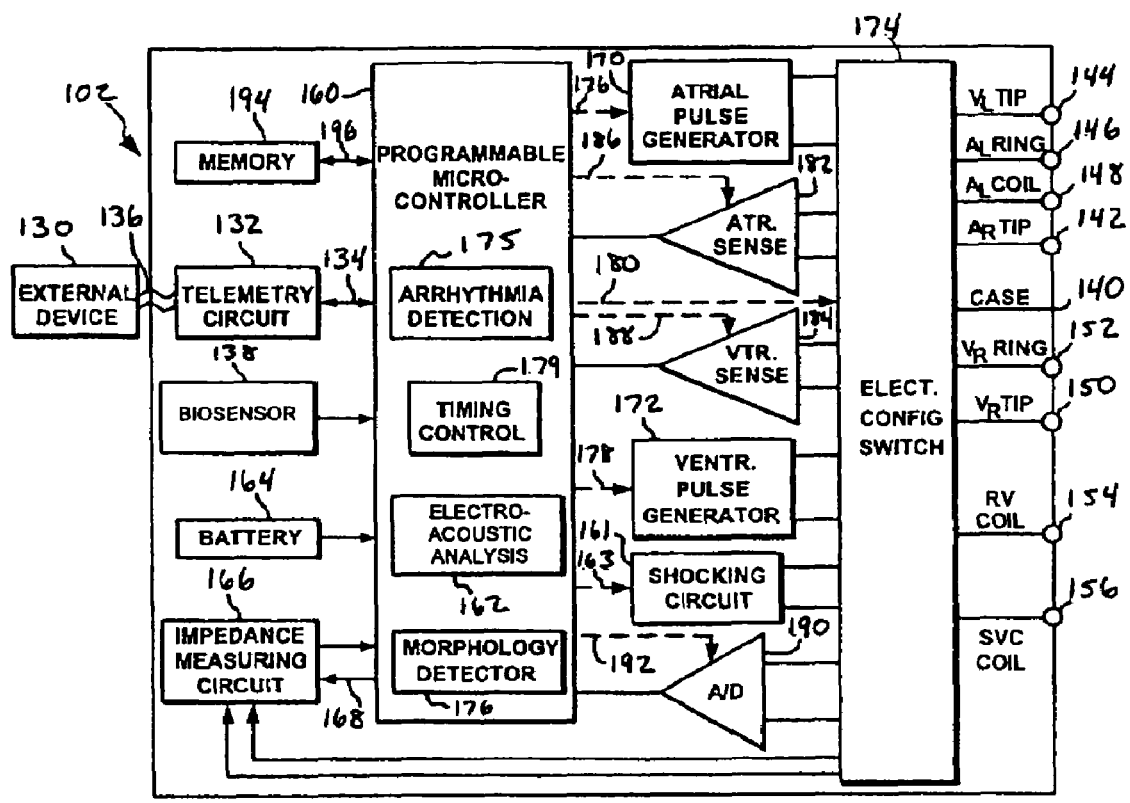
FIG. 1B is a block diagram of the example ICTD of FIG. 1A.

The present invention is particularly useful in the environment of an implantable cardiac therapy device. Implantable cardiac therapy devices include, for example, pacemakers and cardioverter defibrillators. The term "implantable cardiac therapy device," or simply "ICTD," is used herein to refer to any pacemaker or implantable cardioverter defibrillator ("ICD"). FIGS. 1A and 1B illustrate such an environment.

As shown in FIG. 1A, an exemplary ICTD 102 is in electrical communication with a patient's heart 104 by way of three leads, 106, 108 and 110, suitable for delivering multi-chamber stimulation and pacing therapy. To sense atrial cardiac signals and to provide right atrial chamber stimulation therapy, ICTD 102 is coupled to implantable right atrial lead 106 having at least an atrial tip electrode 112, which typically is implanted in the patient's right atrial appendage.

To sense left atrial and ventricular cardiac signals and to provide left-chamber pacing therapy, ICTD 102 is coupled to "coronary sinus" lead 108 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 108 is designed to receive atrial and ventricular cardiac signals and to deliver left ventricular pacing therapy using at least a left ventricular tip electrode 114, left atrial pacing therapy using at least a left atrial ring electrode 116, and shocking therapy using at least a left atrial coil electrode 118.

ICTD 102 is also shown in electrical communication with the patient's heart 104 by way of an implantable right ventricular lead 110 having a right ventricular tip ("RV") electrode 120, a RV ring electrode 122, a RV coil electrode 124, and a superior vena cava ("SVC") coil electrode 126. Typically, right ventricular lead 110 is transvenously inserted into heart 104 so as to place the RV tip electrode 120 in the right ventricular apex so that RV coil electrode 124 will be positioned in the right ventricle and SVC coil electrode 126 will be positioned in the superior vena cava. Accordingly, right ventricular lead 110 is capable of receiving cardiac signals and delivering stimulation in the form of pacing and shock therapy to the right ventricle.

FIG. 1B shows a simplified block diagram of ICTD 102, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

ICTD 102 is shown schematically in FIG. 1B. Housing 140 is often referred to as the "can," "case" or "case electrode" and may be programmably selected to act as the return electrode for all "unipolar" modes. Housing 140 may further be used as a return electrode alone or in combination with one or more of coil electrodes 118, 124, and 126 for shocking purposes. Housing 140 further includes a connector (not shown) having a plurality of terminals, 142, 144, 146, 148, 150, 152, 154, and 156 (shown schematically and, for convenience, the names of the electrodes to which they are connected are shown next to the terminals). As such, to achieve right atrial sensing and pacing, the connector includes at least a right atrial tip terminal ($A_R$ TIP) 142 adapted for connection to atrial tip electrode 112.

To achieve left chamber sensing, pacing and shocking, the connector includes at least a left ventricular tip terminal ($V_L$ TIP) 144, a left atrial ring terminal ($A_L$ RING) 146, and a left atrial shocking terminal ($A_L$ COIL) 148, which are adapted for connection to left ventricular ring electrode 114, left atrial tip electrode 116, and left atrial coil electrode 118, respectively.

To support right chamber sensing, pacing, and shocking the connector also includes a right ventricular tip terminal ($V_R$ TIP) 150, a right ventricular ring terminal ($V_R$ RING) 152, a right ventricular shocking terminal (RV COIL) 154, and an SVC shocking terminal (SVC COIL) 156, which are configured for connection to RV tip electrode 120, RV ring electrode 122, RV coil electrode 124, and SVC coil electrode 126, respectively.

At the core of ICTD 102 is a programmable microcontroller 160 which controls the various modes of stimulation therapy. As is well known in the art, microcontroller 160 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 160 includes the ability to process or monitor input signals (data) as controlled by a program code stored in a designated block of memory. The details of the design of microcontroller 160 are not critical to the present invention. Rather, any suitable microcontroller 160 can be used to carry out the functions described herein. The use of microprocessor-based control circuits for performing timing and data analysis functions are well known in the art. In a specific embodiment of the present invention, however, microprocessor 160 has an electroacoustic analysis circuitry block 162 for analyzing electroacoustic data.

Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the ICTD's and their inter-relationship, see U.S. Pat. No. 4,788,980 (Mann et al. et al.). The '052, '555, '298 and '980 patents are incorporated herein by reference.

As shown in FIG. 1B, an atrial pulse generator 170 and a ventricular pulse generator 172 generate pacing stimulation pulses for delivery by right atrial lead 106, right ventricular lead 110, and/or coronary sinus lead 108 via an electrode configuration switch 174. It is understood that in order to provide stimulation therapy in each of the four chambers of the heart, atrial and ventricular pulse generators 170 and 172 may include dedicated, independent pulse generators, multiplexed pulse generators, or shared pulse generators. Pulse generators 170 and 172 are controlled by microcontroller 160 via appropriate control signals 176 and 178, respectively, to trigger or inhibit the stimulation pulses. Power for the microcontroller 160, as well as for the various pulse generators, is supplied by a battery 164.

Microcontroller 160 further includes timing control circuitry 179 which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) interval, interatrial (RA-LA) interval, and pacing rate.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar, etc.) by selectively closing the appropriate combination of switches (not shown) as is known in the art.

Atrial sensing circuit 182 and ventricular sensing circuit 184 may also be selectively coupled to right atrial lead 106, coronary sinus lead 108, and right ventricular lead 110 through switch 174 for detecting the presence of cardiac activity in each of the four chambers of the heart. Accordingly, the atrial (ATR. SENSE) and ventricular (VTR. SENSE) sensing circuits 182 and 184 may include dedicated sense amplifiers, multiplexed amplifiers, or shared amplifiers. Switch 174 determines the "sensing polarity" of the cardiac signal by selectively closing the appropriate switches, as is also known in the art. In this way, a clinician may program the sensing polarity independent of the stimulation polarity.

Each sensing circuit 182 and 184 preferably employs one or more low power precision amplifiers with programmable gain and/or automatic gain control, bandpass filtering, and a threshold detection circuit, as known in the art, to selectively sense the cardiac signal of interest. The automatic gain control enables ICTD 102 to deal effectively with the difficult problem of sensing the low amplitude signal characteristics of atrial or ventricular fibrillation.

The outputs of atrial and ventricular sensing circuits 182 and 184 are connected to microcontroller 160 which, in turn, is able to trigger or inhibit atrial and ventricular pulse generators, 170 and 172, respectively, in a demand fashion in response to the absence or presence of cardiac activity, in the appropriate chambers of the heart. Sensing circuits 182 and 184, in turn, receive control signals over signal lines 186 and 188 from microcontroller 160 for purposes of measuring cardiac performance at appropriate times, and for controlling the gain, threshold, polarization charge removal circuitry (not shown), and timing of any blocking circuitry (not shown) coupled to the inputs of sensing circuits 182 and 186.

For arrhythmia detection, ICTD 102 utilizes the atrial and ventricular sensing circuits 182 and 184 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by microcontroller 160 by comparing them to a predefined rate zone limit (i.e., bradycardia, normal, low rate VT, high rate VT, and fibrillation rate zones) and various other characteristics (e.g., sudden onset, stability, physiologic sensors, morphology, etc.) in order to determine the type of remedial therapy that is needed (e.g., bradycardia pacing, anti-tachycardia pacing, cardioversion shocks or defibrillation shocks, collectively referred to as "tiered therapy"). According to the present invention, electroacoustic analysis provides an additional source of information for optimization of ICTD performance for arrhythmia therapy.

Microcontroller 160 utilizes arrhythmia detection circuitry 175 and morphology detection circuitry 176, as well as, in the present invention, electroacoustic analysis circuitry 162, to recognize and classify arrhythmias so that appropriate therapy can be delivered.

Cardiac signals are also applied to the inputs of an analog-to-digital (A/D) data acquisition system 190. Data acquisition system 190 is configured to acquire intracardiac electrogram signals, convert the raw analog data into a digital signal, and store the digital signals for later processing and/or telemetric transmission to an external device 130. Data acquisition system 190 is coupled to right atrial lead 106, coronary sinus lead 108, and right ventricular lead 110 through switch 174 to sample cardiac signals across any pair of desired electrodes.

Data acquisition system 190 can be coupled to microcontroller 160, or other detection circuitry, for detecting an evoked response from heart 104 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 160 detects a depolarization signal during a window following a stimulation pulse, the presence of which indicates that capture has occurred. Microcontroller 160 enables capture detection by triggering ventricular pulse generator 172 to generate a stimulation pulse, starting a capture detection window using timing control circuitry 179 within microcontroller 160, and enabling data acquisition system 190 via control signal 192 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al. et al.); and U.S. Pat. No. 5,350,410 (Kleks et al.), which patents are hereby incorporated herein by reference. The type of capture detection system used is not critical to the present invention.

Microcontroller 160 is further coupled to a memory 194 by a suitable data/address bus 196, wherein the programmable operating parameters used by microcontroller 160 are stored and modified, as required, in order to customize the operation of ICTD 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 104 within each respective tier of therapy.

The operating parameters of ICTD 102 may be non-invasively programmed into memory 194 through a telemetry circuit 132 in telemetric communication with external device 130, such as a programmer, transtelephonic transceiver, or a diagnostic system analyzer. Telemetry circuit 132 is activated by microcontroller 160 by a control signal 134. Telemetry circuit 132 allows intracardiac electrograms and status information relating to the operation of ICTD 102 (as contained in microcontroller 160 or memory 194) to be sent to external device 130 through an established communication link 136.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

Telemetry circuit 132 also allows optimization parameters obtained externally to be sent into microcontroller 160. For example, in the present invention, electroacoustic data may be obtained by an external or transcutaneous electroacoustic device. That data may be assessed by a physician during a patient visit, and on the direction of the physician could be transmitted to microcontroller 160 for analysis and optimization of a number of parameters, as discussed below. Analysis may also be completed externally at a physician's office, with instructions based on the analysis transmitted to microcontroller 160.

In an embodiment of the present invention, ICTD 102 further includes a biosensor 138 that can detect electroacoustic changes indicative of cardiac performance or changes in the physiological condition of the heart. ICTD 102 also includes electroacoustic analysis circuitry 162. Electroacoustic analysis circuitry 162 can be implemented in hardware, software, or firmware. Electroacoustic analysis circuitry 162 may be located in microcontroller 160, as depicted, or it can be separate from microcontroller 160. Accordingly, microcontroller 160 can respond by adjusting the various pacing parameters (such as rate, AV Delay, RV-LV interval, etc.) in accordance with the embodiments of the present invention. Microcontroller 160 controls adjustments of pacing parameters by, for example, controlling the stimulation pulses generated by the atrial and ventricular pulse generators 170 and 172. While shown in FIG. 1A as being included within ICTD 102, one skilled in the art will recognize that biosensor 138 may also be external to ICTD 102 while implanted within or carried by a patient and still send information to microcontroller 160. More specifically, biosensor 138 can be located inside ICTD 102, on the surface of ICTD 102, in a header of ICTD 102, on a lead (which can be placed inside or outside the bloodstream), or otherwise separated from ICTD 102. Further details on possible locations for biosensor 138 will be discussed below with respect to FIG. 4.

ICTD 102 further includes a magnet detection circuitry (not shown), coupled to microcontroller 160. It is the purpose of the magnet detection circuitry to detect when a magnet is placed over ICTD 102, which magnet may be used by a clinician to perform various test functions of ICTD 102 and/or to signal microcontroller 160 that the external programmer 130 is in place to receive or transmit data to microcontroller 160 through telemetry circuit 132.

As further shown in FIG. 1B, ICTD 102 includes an impedance measuring circuit 166 which is enabled by microcontroller 160 via a control signal 168. The known uses for an impedance measuring circuit 166 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 166 is advantageously coupled to switch 174 so that any desired electrode may be used. The impedance measuring circuit 166 is not critical to the present invention and is shown only for completeness.

In the case where ICTD 102 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 160 further controls a shocking circuit 161 by way of a control signal 163. The shocking circuit 161 generates shocking pulses of low (up to 0.5 Joules), moderate (0.5-10 Joules), or high energy (11 to 40 Joules), as controlled by microcontroller 160. Such shocking pulses are applied to the patient's heart 104 through at least two shocking electrodes (e.g., selected from left atrial coil electrode 118, RV coil electrode 124, and SVC coil electrode 126). As noted above, housing 140 may act as an active electrode in combination with RV electrode 124, or as part of a split electrical vector using SVC coil electrode 126 or left atrial coil electrode 118 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of fibrillation. Accordingly, microcontroller 160 is capable of controlling the synchronous or asynchronous delivery of the shocking pulses.

B. Electroacoustics

Figure 2A:
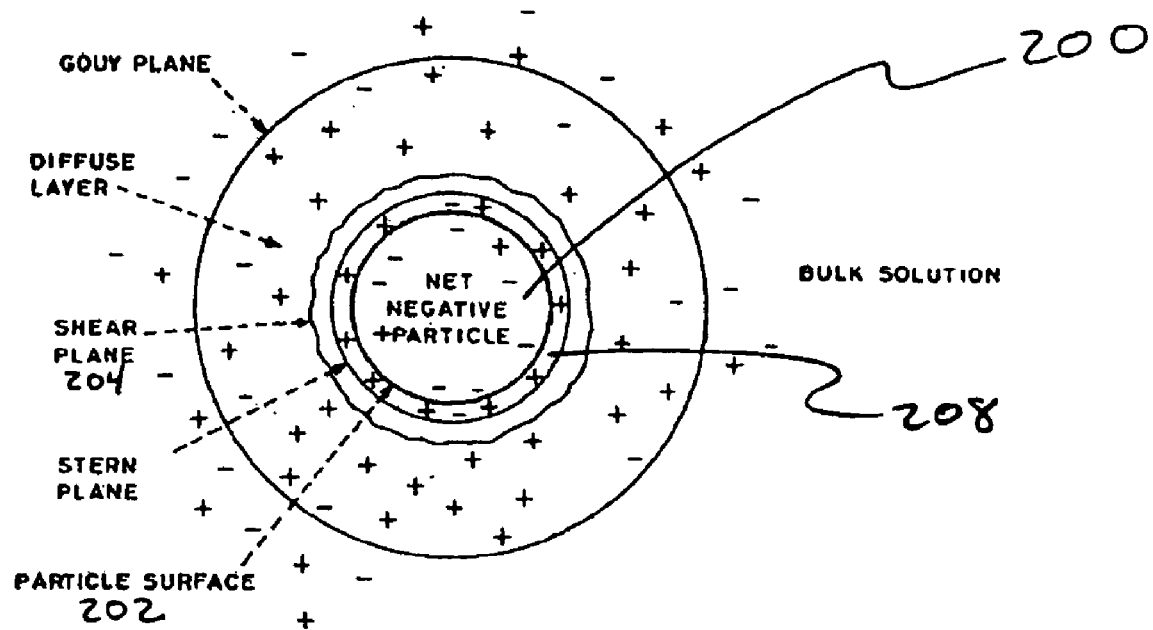
FIG. 2A is an illustration of a colloid double layer in a steady state arrangement.

FIG. 2A illustrates how the ions in a colloid organize themselves relative to a suspended particle 200. FIG. 2A shows particle 200 in a steady state. Particle surface 202 is represented by the innermost ring. Because of the affinity of ions for a surface, an electric surface charge builds up and creates an electrostatic field. Alternatively, the surface charge of the particle may be fixed. See, A. S. Dukhin & P. J. Goetz, *Ultrasound for Characterizing Colloids: Particle Sizing, Zeta Potential, Rheology* (Elsevier 2002), hereby incorporated by reference herein in its entirety. This electrostatic field affects ions in the liquid surrounding particle 200. This draws ions in the liquid toward the particle and results in what is referred to as a "double layer". The first layer of the double layer is particle surface 202. The second layer 208 is made up of oppositely charged ions from the surrounding liquid held in close association to the ions in the particle. The outer boundary of the double layer is the shear plane 204.

Figure 2B:
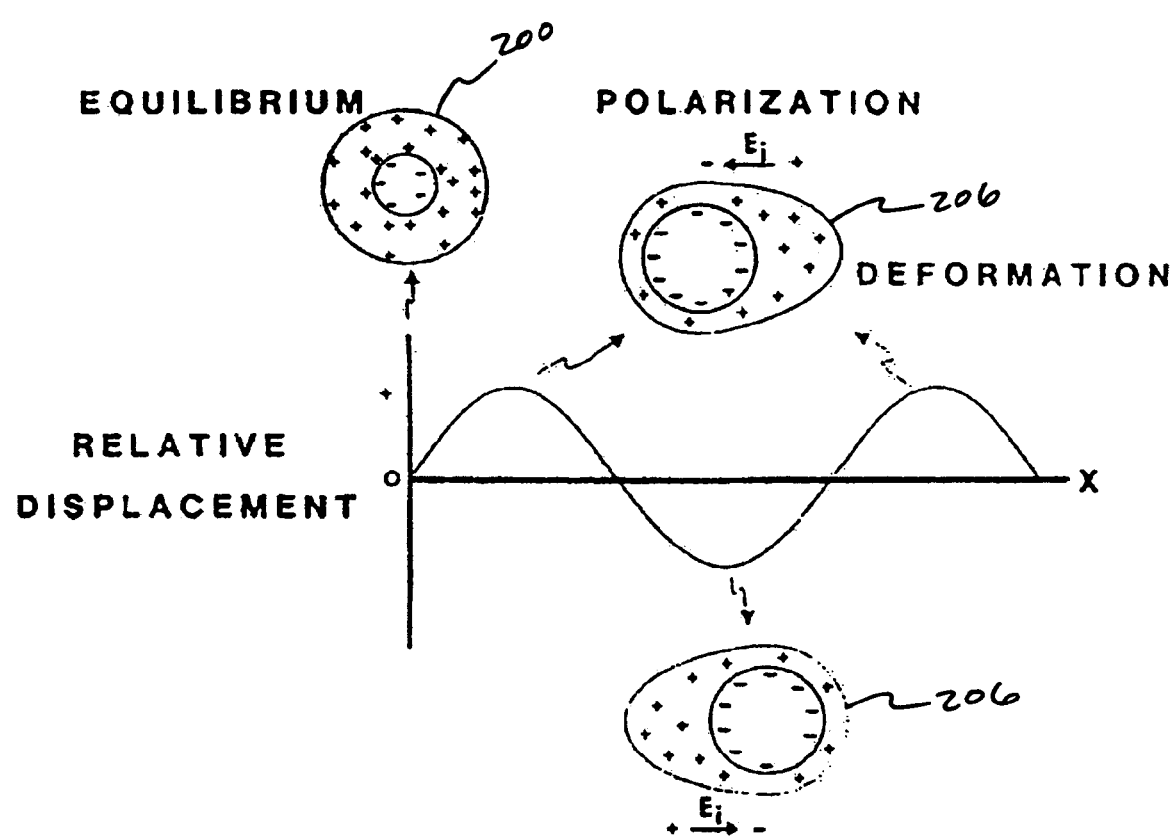
FIG. 2B is an illustration of colloid double layer distortions caused by an assaulting field.

FIG. 2B shows the effect of an acoustic or time-varying electric assaulting field on particle 200. Before the assaulting field is applied, at time t=0, the double layer of particle 200 is in a steady state arrangement, or equilibrium. In response to the assaulting field, the charged particle and the surrounding double layer are displaced relative to their mass/density. The difference in density between them disrupts the double layer. A representation of this shift is shown as disrupted particle 206. When the assaulting field is removed, the molecules in second layer 208 return to the steady state arrangement. This movement of molecules returning to steady state emits a resultant field which can be detected. If the assaulting field is acoustic, the resultant field is electric. Likewise, if the assaulting field is electric, the resultant field is acoustic.

C. Biosensor

Biosensor 138 is configured to transmit and detect acoustic and/or electric energy. An ultrasound probe used in inorganic colloidal chemistry is described in Dukhin & Goetz, pp. 235-237. The biosensor of the present invention utilizes a probe similar to that described in Dukhin & Goetz. Although the present invention will be described with reference to the probe discussed in Dukhin & Goetz, it will be apparent to one skilled in the art that other probes with different geometries and dimensions for detecting colloidal concentrations may be used. Other example probes for use in the present invention are the DT300, DT100, and DT1200 manufactured by Dispersion Technology, Inc., of Bedford Hills, N.Y., which produce an acoustic field and measure an electric field, and the ESA9800 manufactured by Matec Applied Sciences, of Northborough, Mass., which produces an electric field and measures an acoustic field.

Figure 3A:
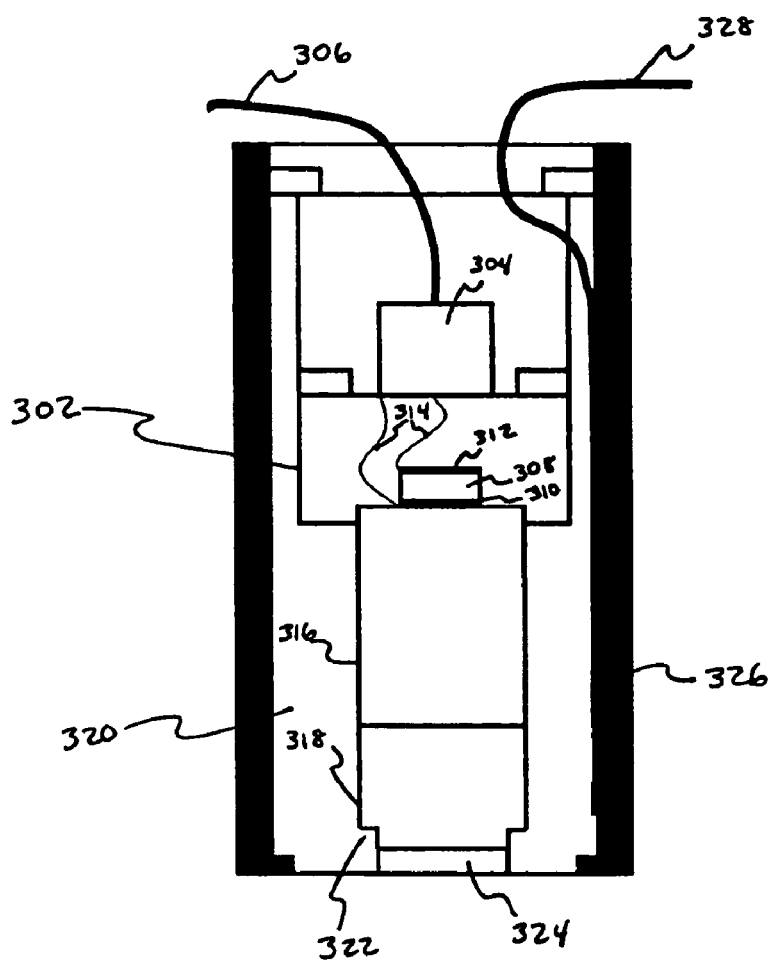
FIG. 3A is a block diagram of an example probe used in the present invention.

FIG. 3A is a block diagram of an exemplary probe 300. A transmitting portion of probe 300 includes a transducer 302, connected to cable connector 304 and input cable 306. In an embodiment, cable connector 304 is a UHF cable connector. In an embodiment, transducer 302 includes a cylindrical piezoelectric device 308 having a front electrode 310 and a back electrode 312 across which an RF pulse can be applied to generate an acoustic assaulting pulse. A person of ordinary skill in the art will recognize, however, that other types of transducers may be used, such as transducers with non-piezoelectric materials or transducers of varying sizes and shapes. Further, although FIG. 3A is described herein with reference to generation of an acoustic assaulting field, one skilled in the art will recognize that a similar device may be employed to generate an electric assaulting field. Front electrode 310 and back electrode 312 of piezoelectric device 308 are connected to corresponding terminals of connector 304 by means of internal jumper wires 314 in a manner well known to those skilled in the art. Piezoelectric device 308 in turn is bonded to a delay rod 316 by means of a suitable adhesive. In an embodiment, delay rod 316 is formed out of quartz.

The resonant frequency of piezoelectric device 308 is selected depending on the frequency range for which electroacoustic data is desired. The present invention detects electroacoustic data for organic compounds such as, for example, proteins, suspended in a liquid such as, for example, blood. In an embodiment, in order to provide an appropriate range for each protein of interest, the present invention scans within a frequency range of about 0.5 MHz to 100 MHz. In another embodiment, the frequency range is about 0.9 MHz to 1.2 MHz.

Delay rod 316 of probe 300 is extended by an additional buffer rod 318 having an acoustic impedance that is closely matched to that of the colloid. Transducer 302 and buffer rod 318 are cemented together and inserted into a ceramic spacer 320 until buffer rod 318 aligns with a shoulder 322 on spacer 320.

Figure 3B:
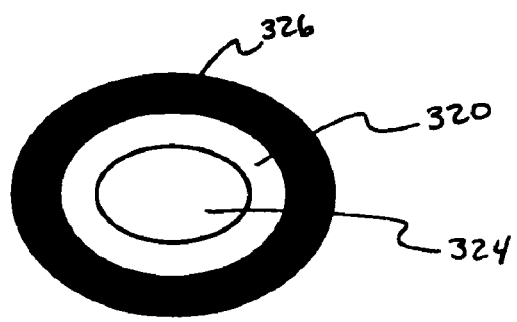
FIG. 3B is an alternative view of the example probe shown in FIG. 3A.

In an embodiment, the end of buffer rod 318 is coated with gold in order to provide an electrode for measuring the electrical response of the colloid when excited acoustically. This electrical response is also referred to herein as the resultant field. FIG. 3B provides an end view of probe 300 showing the relative location of gold electrode 324, spacer 320, and a casing 326.

A coaxial cable 328 detects the resultant field once the assaulting field is turned off. In an embodiment where the assaulting field is an acoustic field, the resultant field is detected as a colloid vibration current ("CVI") signal. In another embodiment, where the assaulting field is an electric field, the resultant field is detected as an electrosonic amplitude ("ESA") signal. When probe 300 comes in contact with the colloid, the signal between gold electrode 324 and the surrounding casing 326 is thus available at the output of coaxial cable 328.

In an embodiment, biosensor 138 is an implantable biosensor controlled by electroacoustic analysis circuitry 162 in ICTD 102. Biosensor 138 may be implanted in one of several locations. In one embodiment, biosensor 138 is implanted in the vicinity of a blood vessel in the body and generates an electric or acoustic assaulting field directed at that blood vessel. In another embodiment, biosensor 138 is implanted in interstitial fluid.

Figure 4:
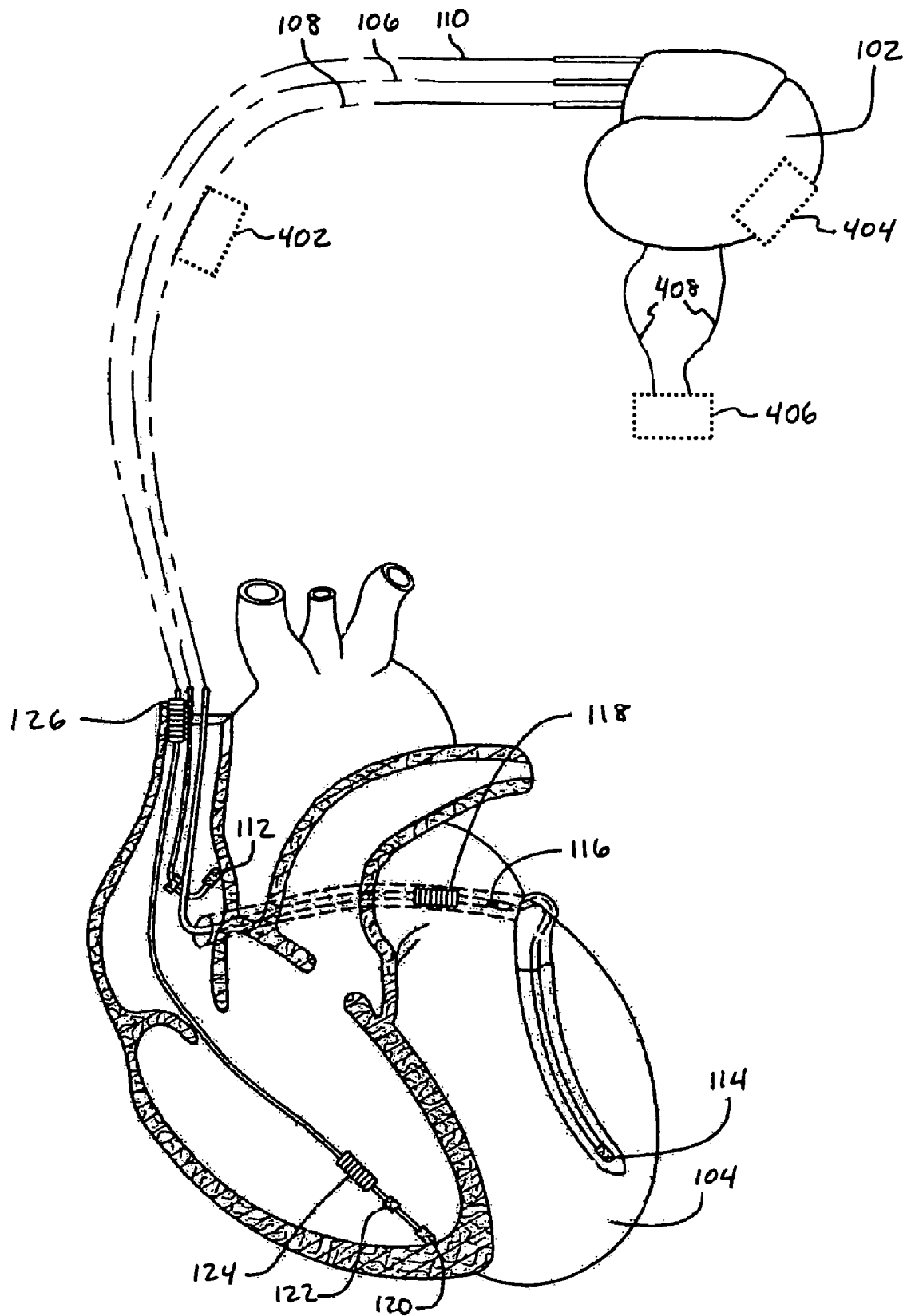
FIG. 4 is a diagram of example locations for an implantable biosensor of the present invention.

FIG. 4 illustrates example locations for biosensor 138 (not shown to scale) with respect to ICTD 102. In one embodiment, biosensor 138 is connected at location 402 to the surface of a lead of ICTD 102, such as leads 106, 108, or 110. In another embodiment, biosensor 138 is attached at location 404 to housing 140 of ICTD 102. In yet another embodiment, biosensor 138 is placed at location 406 in extravascular space outside a blood vessel, and is connected to ICTD 102 through connecting wires or transmission lines 408. Alternatively, biosensor 138 may transmit information to ICTD 102 wirelessly.

Biosensor 138 may also interact transcutaneously with substances in the body. In this embodiment, biosensor 138 transmits an assaulting field through the skin from an external location to disrupt a colloid in the body. In another embodiment, biosensor 138 is a standalone sensor used to detect substances in biological liquids. For example, biosensor 138 can be used to detect protein levels in a blood sample.

Figure 5:
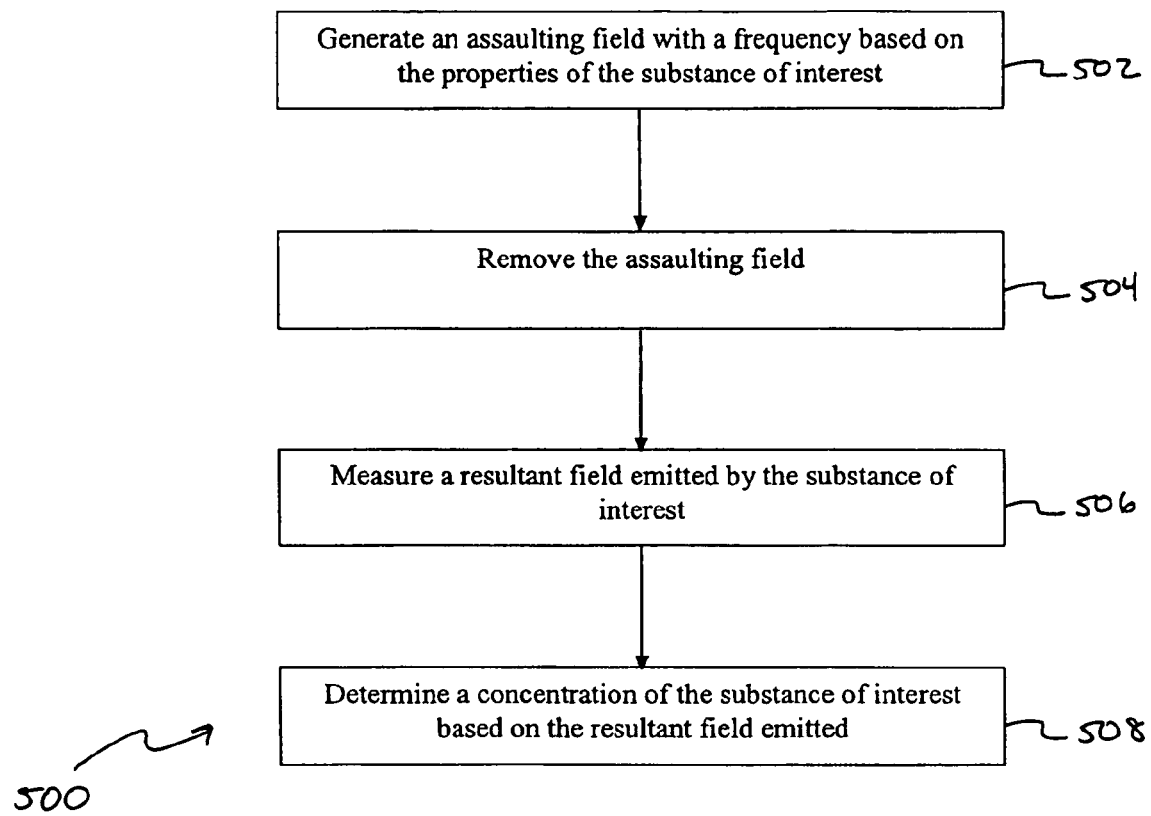
FIG. 5 is a flowchart of an embodiment of the present invention.

FIG. 5 is a flowchart of a method 500 used in the present invention. In step 502, an assaulting field is produced either in vivo or transcutaneously. In one embodiment, the assaulting field is an acoustic field. In another embodiment, the assaulting field is an electric field. The frequency of the assaulting field is chosen based on the properties of the substance of interest. In one embodiment, the substance of interest is the protein ANP and/or BNP. In another embodiment, the substance of interest is at least one of the following: C-reactive protein, CK-MB, Troponin I, Troponin T, Troponin C, or myoglobin. One or more protein concentrations may be sought after at one time. The assaulting field may be directed at the substance in a blood vessel, or at the substance in interstitial fluid. As described above with respect to FIG. 2B, the assaulting field disrupts the double layer of particles in the direction of the field.

In step 504, the assaulting field is removed. At this point, the ions reassemble the double layer and give off an in vivo resultant field proportional to the energy required for the initial disruption of the ions. This resultant field is measured in step 506.

In step 508, the concentration of the substance of interest is determined based on the resultant field measured in step 506. In an embodiment, the measurements of the resultant field are transmitted to the electroacoustic analysis circuitry 162, for determination by the ICTD 102. In another embodiment, the measurements are transmitted to external device 130 to determine the concentration.

Method 500 may also be used for an external biosensor. In this embodiment, the assaulting field is directed in step 502 toward proteins in an external blood sample. All other steps in method 500 remain the same.

In an embodiment, method 500 is repeated continuously. In another embodiment, method 500 is repeated periodically. In yet another embodiment, the repeat cycle of method 500 is synchronized to the cardiac cycle to account for changes in cross-sectional area of the vessel. In another embodiment, the repeat cycle of method 500 is synchronized to the respiratory cycle to account for subtle changes in blood pH which influence the isoelectric potential of proteins. In still another embodiment, the repeat cycle of method 500 is synchronized to an activity sensor to account for motion and greater change in blood pH as $O_2$ and $CO_2$ levels shift during maximal exercise. Method 500 may be used as a monitoring technique by clinicians, wherein the relative levels of substances in the blood are indicative of cardiac health.

Figure 6:
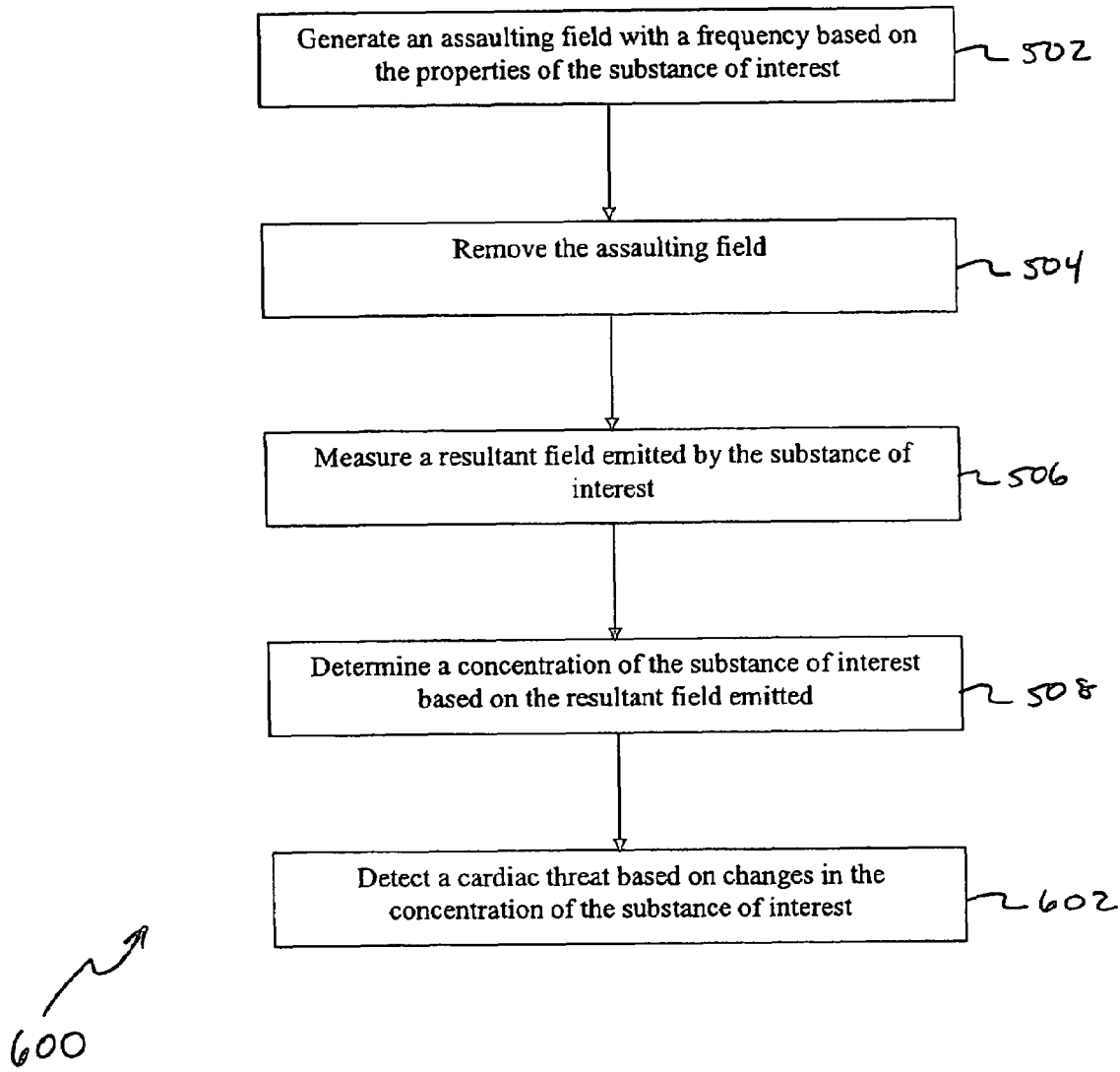
FIG. 6 is another flowchart of an embodiment of the present invention.

FIG. 6 is a flowchart of a method 600, wherein an additional step is added to method 500. In step 602, a cardiac threat is detected based on changes in the concentration of the substance of interest. For example, concentration levels of BNP and/or ANP can provide early warning of an impending heart failure exacerbation. Alternatively, concentration levels of C-reactive protein, CK-MB, Troponin I, Troponin T, Troponin C, and/or myoglobin can provide early warning of an myocardial ischemia and impending arrhythmia.

Step 602 is performed by an interpreter, such as, for example, microcontroller 160. In an embodiment, microcontroller 160 performs step 602 by interpreting data from biosensor 138. For example, microcontroller 160 can compare protein concentrations to one or more predetermined thresholds and then take action based on the results of the comparisons. In this embodiment, if a cardiac threat has developed, ICTD 102 may be able to initiate therapy based on the data received. In another embodiment, an external device or clinician may perform step 602.

D. Experimental Results

Figure 7:
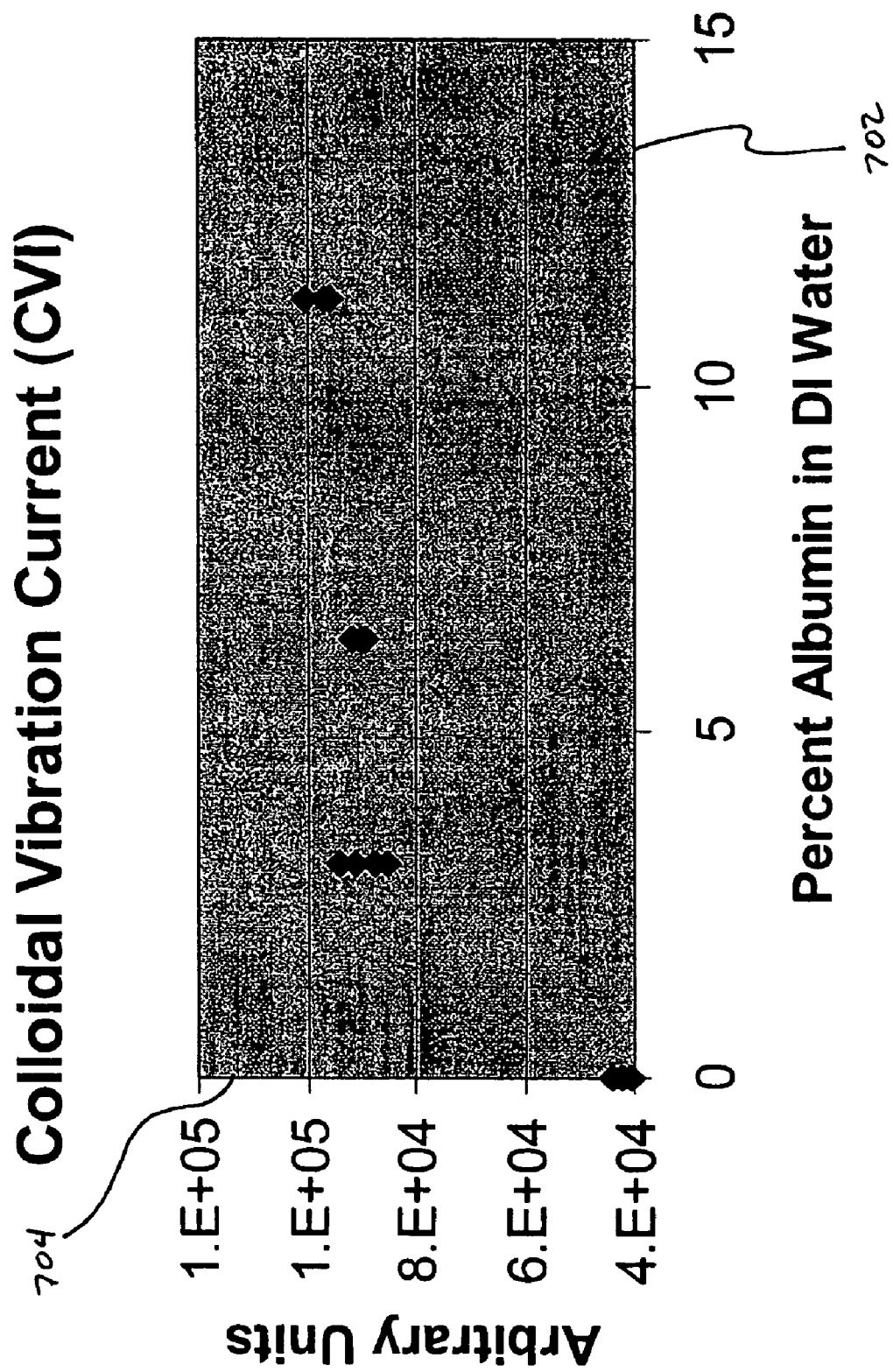
FIG. 7 is a graph of colloidal vibration current ("CVI") resulting from various concentrations of albumin in deionized water.

FIG. 7 is a graph of test results obtained when using an acoustic assaulting field from a stand-alone Dispersion Technologies device to detect levels of albumin in deionized water. The assaulting field had a field strength of 10 mW and a frequency of 3 MHz. The albumin slowly dissolved into the deionized water as the water was warmed. Several samples of varying concentrations were taken. These concentrations are shown on horizontal axis 702. A uniform acoustic field was applied to all samples. The magnitude of the electric resultant field detected (i.e., colloidal vibration current or CVI) is shown on vertical axis 704. As shown by the various data points, the detected CVI changed as the colloidal composition changed.

Figure 8:
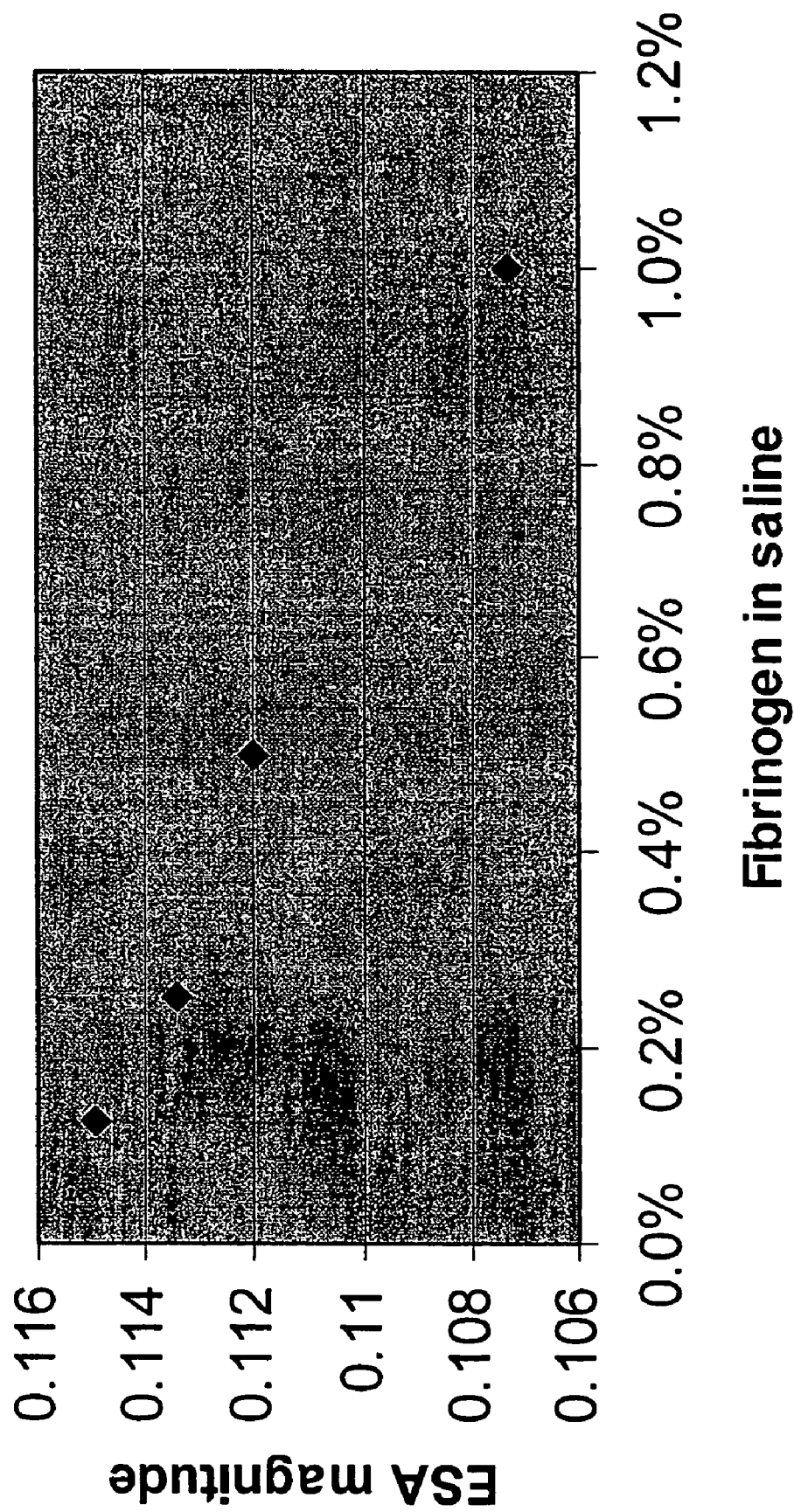
FIG. 8 is a graph of electrosonic amplitude ("ESA") resulting from various concentrations of fibrinogen in saline.
Figure 9:
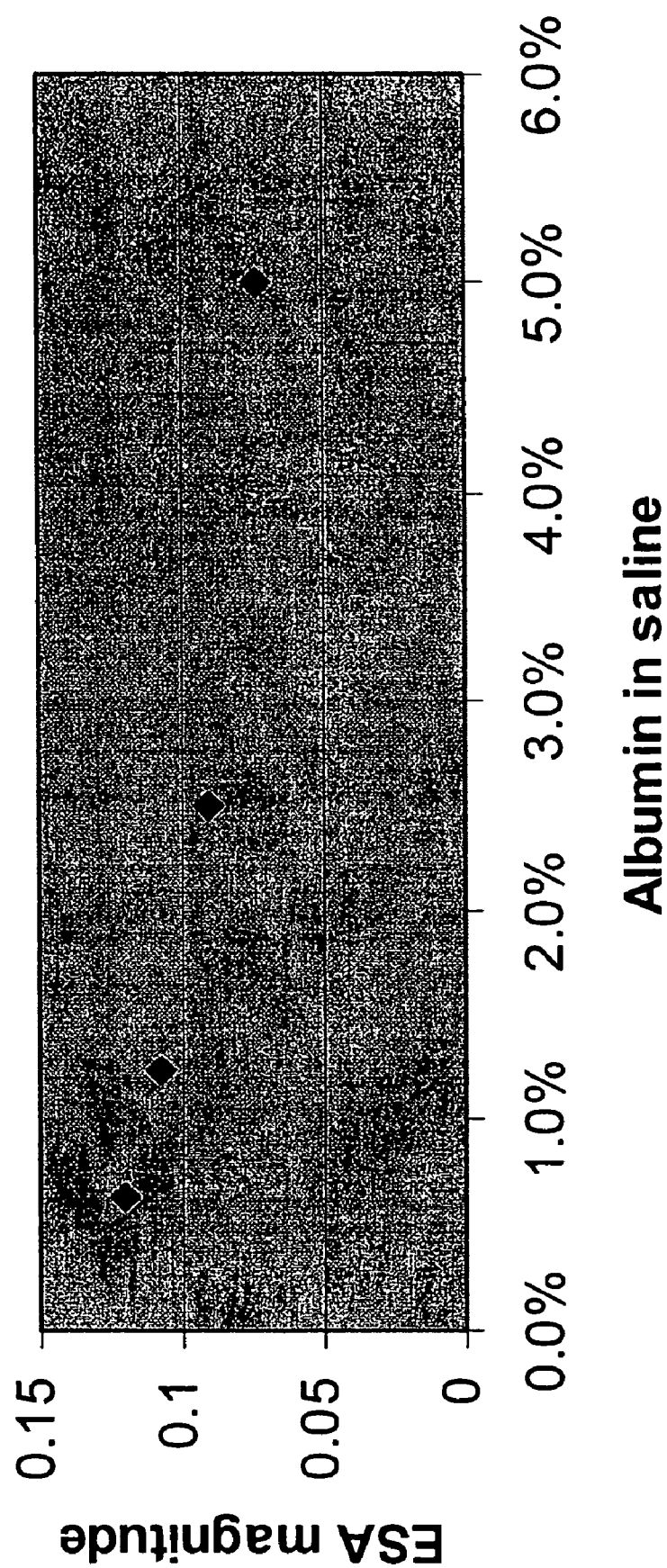
FIG. 9 is a graph of ESA resulting from various concentrations of albumin in saline.
Figure 10:
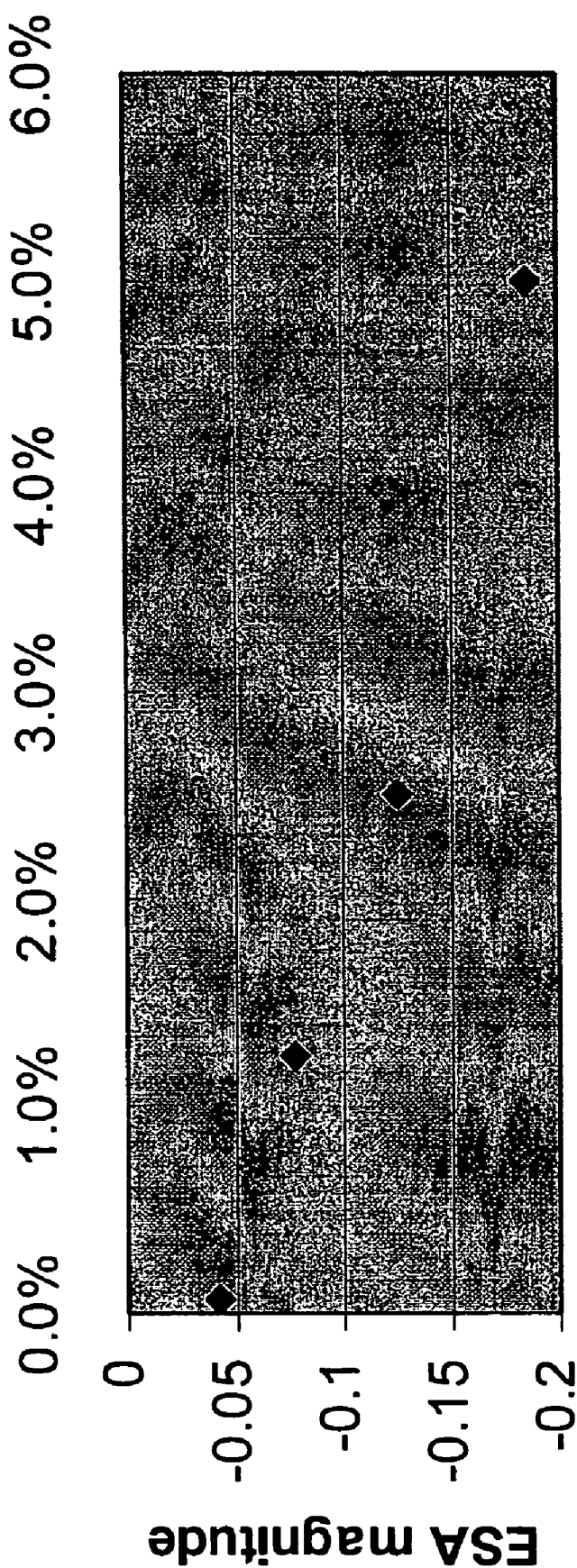
FIG. 10 is a graph of ESA resulting from various concentrations of albumin in deionized water.
Figure 11:
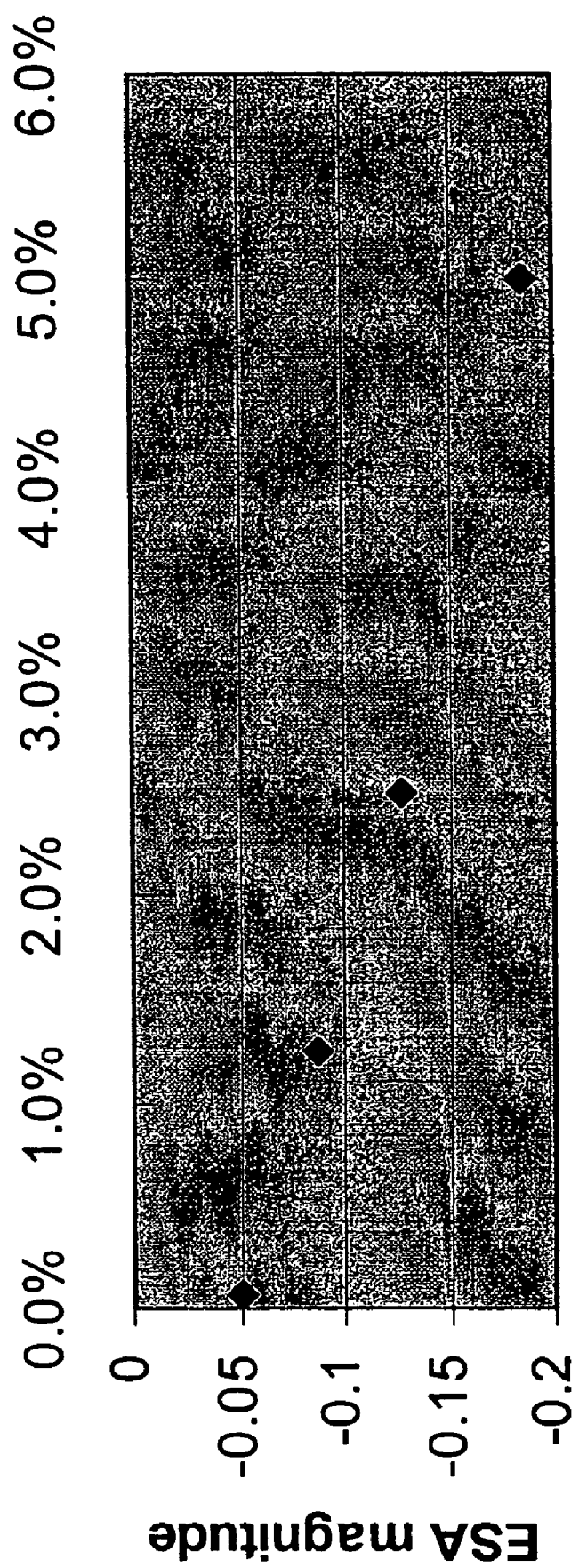
FIG. 11 is a graph of ESA resulting from various concentrations of albumin in deionized water.

Each of FIGS. 8-11 displays results from tests in which the assaulting field was a time-varying electric field created by a stand-alone Matec Applied Sciences device. The sinusoidal electric field had a field strength of approximately 66 V/mm and a frequency of approximately 1 MHz. The process of testing samples was analogous to the process described with respect to FIG. 7. In each figure, the varying concentrations of the colloid are displayed on the horizontal axis, with the magnitude of the corresponding acoustic resultant field (e.g., ESA) on the vertical axis. The assaulting field was constant for testing all samples of each colloid. FIG. 8 displays ESA magnitude resulting from various concentrations of Fibrinogen in saline. FIG. 9 displays ESA magnitude resulting from various concentrations of albumin in saline. FIGS. 10 and 11 display ESA magnitude resulting from two separate tests of various concentrations of albumin in deionized water. The results of the tests in FIG. 10 and FIG. 11 are very similar, which shows the accuracy of the method. As shown in FIGS. 8-11, the magnitude of the resultant field varies nearly linearly with concentration.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A method of monitoring a concentration of suspended particles in a biomedical colloid comprising:
   a. producing an assaulting acoustic field;
   b. measuring a resultant electric field produced in vivo by particle interaction with the assaulting field; and
   c. determining the concentration of the suspended particles based on the measured resultant field.

2. The method of claim 1, wherein said biomedical colloid is blood.

3. The method of claim 1, wherein said biomedical colloid is interstitial fluid.

4. The method of claim 1, wherein said suspended particles are proteins.

5. The method of claim 4, further comprising:
   d. assessing a cardiac threat based on the concentration of the suspended proteins.

6. The method of claim 5, wherein said suspended proteins include at least one of the group consisting of BNP and ANP.

7. The method of claim 6, wherein said cardiac threat is heart failure exacerbation.

8. The method of claim 5, wherein said suspended proteins comprise at least one protein selected from the group consisting of C-reactive protein, CK-MB, ischemia-modified albumin, Troponin I, Troponin T, Troponin C, and myoglobin.

9. The method of claim 8, wherein said cardiac threat is at least one of myocardial ischemia and myocardial damage.

10. The method of claim 5, further comprising:
    e. performing cardiac therapy based on the cardiac threat determined in step (d).

11. The method of claim 1, wherein a frequency of said assaulting acoustic field is determined based on properties of the suspended particles.

12. The method of claim 1, further including the step of monitoring changes in the concentration of the suspended particles over time.

13. A method of monitoring a concentration of suspended proteins in a biomedical colloid, comprising:
   a. producing an assaulting field;
   b. measuring a resultant field produced by particle interaction with the assaulting field, wherein one of said assaulting field and said resultant field is an electric field; and
   c. determining the concentration of suspended proteins based on the measured resultant field.

14. The method of claim 13, wherein said biomedical colloid is blood.

15. The method of claim 13, wherein said biomedical colloid is interstitial fluid.

16. The method of claim 13, further comprising:
   d. detecting a cardiac threat based on the concentration of the suspended proteins.

17. The method of claim 16, further comprising:
   e. performing cardiac therapy based on the cardiac threat determined in step (d).

18. The method of claim 13 wherein the other of said assaulting field and said resultant field is an acoustic field.

19. An implantable cardiac therapy device including an implantable biosensor for monitoring a concentration of suspended particles in a biomedical colloid, said implantable biosensor comprising:
   a generator configured to produce an assaulting acoustic field in vivo;
   a transmitter configured to transmit the assaulting acoustic field; and
   a receiver configured to detect a resultant electric field produced in vivo by particle interaction with the assaulting acoustic field, said resultant field being indicative of the concentration of suspended particles.

20. The implantable cardiac therapy device of claim 19, wherein said suspended particles are proteins, and wherein said biomedical colloid is blood.

21. The implantable cardiac therapy device of claim 19, wherein said biomedical colloid is interstitial fluid.

22. The implantable cardiac therapy device of claim 19, wherein said implantable biosensor is configured for implantation in close proximity to a blood vessel.

23. The implantable cardiac therapy device of claim 19, further comprising:
   a processor configured to calculate a concentration of proteins in the biomedical colloid.

24. The implantable cardiac therapy device of claim 23, further comprising:
   an interpreter configured to detect a cardiac threat based on the concentration of proteins.

25. An implantable cardiac therapy device comprising:
   means for producing a first signal, said first signal causing an implantable biosensor to transmit an assaulting field into a biomedical colloid, said assaulting field causing said biomedical colloid to produce a resultant field;
   means for receiving a second signal representative of said resultant field, wherein one of said assaulting field and said resultant field is an electric field; and
   means for processing said second signal to produce a value indicative of a concentration of suspended particles in said biomedical colloid.

26. The implantable cardiac therapy device of claim 25, further comprising:
   means for adjusting a pacing parameter based on said value.

27. The implantable cardiac therapy device of claim 25, wherein said biomedical colloid is blood, wherein said second signal is representative of a concentration of suspended proteins in blood, and wherein said processing means is configured to produce a value indicative of a concentration of suspended proteins in said blood.

28. The implantable cardiac therapy device of claim 27, further comprising:
   means for adjusting a pacing parameter based on said value.

29. The device of claim 25 wherein the other of said assaulting field and said resultant field is an acoustic field.

30. A method of monitoring a concentration of suspended particles in a biomedical colloid comprising:
   a. producing an assaulting electric field;
   b. measuring a resultant field produced in vivo by particle interaction with the assaulting field; and
   c. determining the concentration of the suspended particles based on the measured resultant field.

31. The method of claim 30 wherein the resultant field is an acoustic field.

32. The method of claim 30 and further including the step of storing the determined concentration in a memory.

33. An implantable cardiac therapy device including an implantable biosensor for monitoring a concentration of suspended particles in a biomedical colloid, said implantable biosensor comprising:
   a generator configured to produce an assaulting field in vivo;
   a transmitter configured to transmit the assaulting field; and
   a receiver configured to detect a resultant field produced in vivo by particle interaction with the assaulting field, said resultant field being indicative of the concentration of suspended particles, wherein one of said assaulting field and said resultant field is an electric field.

34. The device of claim 33 wherein the other of said assaulting field and said resultant field is an acoustic field.

* * * * *